(12) United States Patent
Buchmueller

(10) Patent No.: US 8,721,877 B2
(45) Date of Patent: May 13, 2014

(54) UPFLOW REACTOR FEATURING CONTROLLED RECIRCULATION OF BIOMASS

(75) Inventor: Marianne Buchmueller, Uehlingen-Birkendorf (DE)

(73) Assignee: MCB GmbH, Uehlingen-Birkendorf (DE)

( * ) Notice: Subject to any disclaimer, the term of this patent is extended or adjusted under 35 U.S.C. 154(b) by 402 days.

(21) Appl. No.: 13/132,928

(22) PCT Filed: Dec. 4, 2009

(86) PCT No.: PCT/EP2009/008663
§ 371 (c)(1),
(2), (4) Date: Jun. 5, 2011

(87) PCT Pub. No.: WO2010/066379
PCT Pub. Date: Jun. 17, 2010

(65) Prior Publication Data
US 2011/0236274 A1  Sep. 29, 2011

(30) Foreign Application Priority Data
Dec. 10, 2008  (DE) .................. 10 2008 061 461

(51) Int. Cl.
*B01D 35/00* (2006.01)
*B01D 19/00* (2006.01)

(52) U.S. Cl.
USPC ........................ 210/120; 210/188; 210/197

(58) Field of Classification Search
USPC .............. 210/143, 150–151, 188, 195.1, 220, 210/262, 604, 120, 197
See application file for complete search history.

(56) References Cited

U.S. PATENT DOCUMENTS 4,295,795 A * 10/1981 Gass et al. ................. 417/111
7,460,013 B1 * 12/2008 Osborne et al. .............. 340/541

FOREIGN PATENT DOCUMENTS

| DE | 10 2005 050 997 A1 | 5/2007 |
| EP | 0 170 332 A1 | 2/1986 |
| EP | 0 244 029 A1 | 11/1987 |
| EP | 0 300 348 A2 | 1/1989 |
| EP | 0 711 732 A2 | 5/1996 |
| EP | 1 408 008 A1 | 4/2004 |
| WO | WO 99/51532 A1 | 10/1999 |

* cited by examiner

Primary Examiner — Chester Barry
(74) Attorney, Agent, or Firm — ProPat, L.L.C.

(57) ABSTRACT

An upflow reactor is provided that includes a reactor tank, conduits, a waste water distributor, at least one first flotation separator and an optional second flotation separator for separating reactor water, biomass, and biogas, a collection device, and a gas separator for separating biomass and biogas. The first flotation separator includes one or more gas domes that are connected to the collection device and have outlets, the cross-sectional area or geometry of which can be controlled using movable covers.

16 Claims, 6 Drawing Sheets

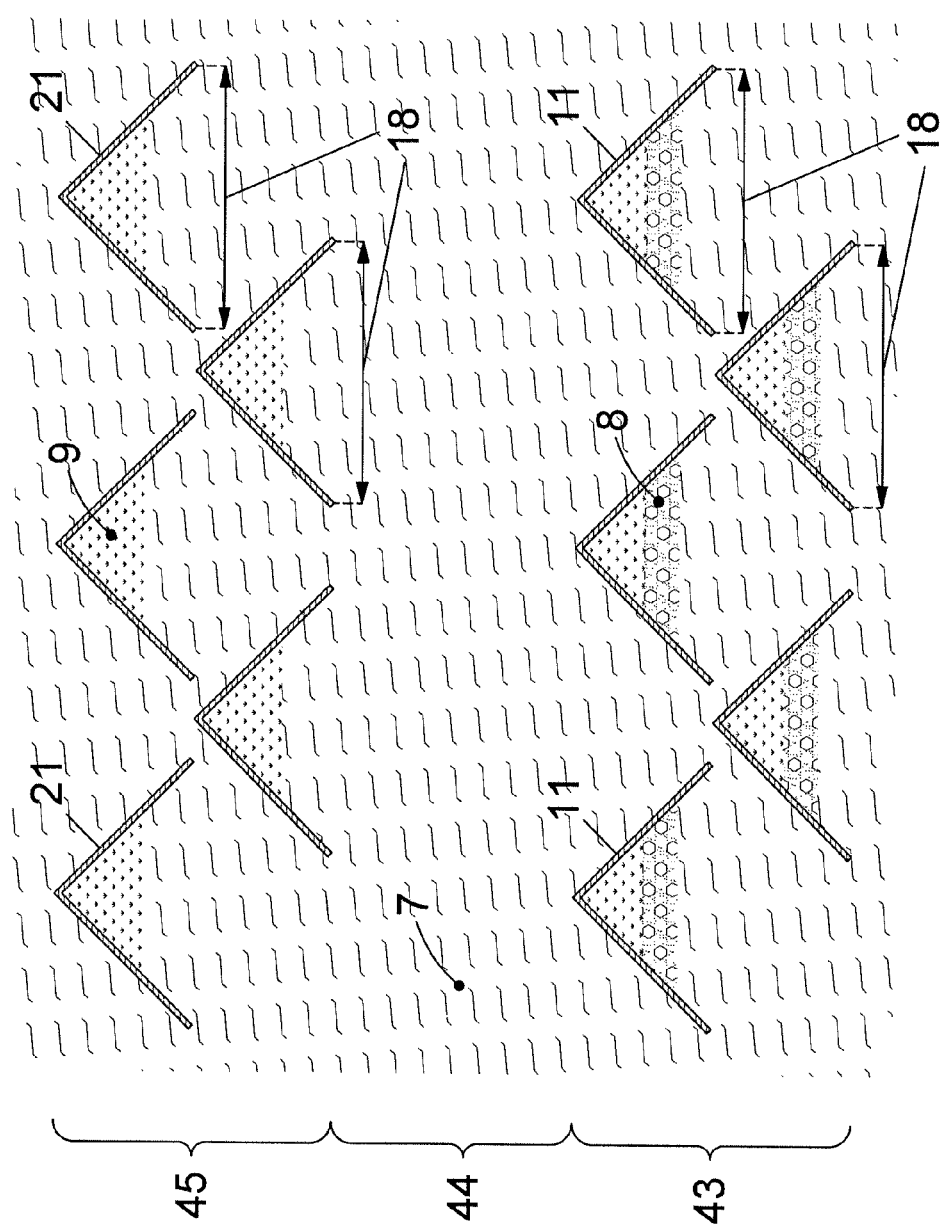

UPFLOW REACTOR FEATURING CONTROLLED RECIRCULATION OF BIOMASS

CROSS-REFERENCE TO RELATED APPLICATIONS

This application is being filed under 35 U.S.C. §371 as a National Stage Application of pending International Application No. PCT/EP2009/008663 filed Dec. 4, 2009, which claims priority to the following parent application: German Patent Application No. 10 2008 061 461.0, filed Dec. 10, 2008. Both International Application No. PCT/EP2009/008663 and German Patent Application No. 10 2008 061 461.0 are hereby incorporated by reference herein in their entirety.

FIELD OF THE INVENTION

The present invention relates to reactors for wash water treatment.

BACKGROUND OF THE INVENTION

The invention relates to an upflow reactor for the biological treatment of waste water. For purifying waste water, a multiplicity of methods are used, inter alia filtration and biological methods which make use of aerobic or anaerobic microorganisms. In particular, waste water that is polluted with organic impurities in dissolved and undissolved form is treated by means of the Upflow Anaerobic Sludge Blanket (UASB) method. The anaerobic sludge blanket of a UASB reactor contains various bacterial species, of which some convert and hydrolyze the undissolved organic impurities to form water-soluble substances—principally organic fatty acids. Subsequently thereto, the dissolved substances are converted to biogas by anaerobic microorganisms present in the sludge blanket, and in this manner the waste water is purified. Biogas is a gas mixture of the components methane and carbon dioxide and also hydrogen sulfide and other trace gases. If sufficient biomass is present for the degradation of the substances present in the water, the optimum hydraulic residence time for the water that is to be purified in the reactor is given by the degree of pollution, expressed, for example, as chemical oxygen demand (COD) and the desired degree of purity. It is known that under favorable conditions, even with hydraulic residence times in the range of a few hours, degrees of purity of greater than 90% are achievable.

However, a high degree of purity may only be achieved in the long term if it is possible to hold a sufficiently large amount of biomass in the reactor or to achieve growth of biomass. The growth rate of anaerobic or aerobic biomass is in the range of approximately $0.05 \cdot d^{-1}$ to $0.5 \cdot d^{-1}$. It must be ensured that at least as much biomass is newly formed in the reactor as is continuously flushed out. In the unfavorable case of high hydraulic throughput with a low COD concentration, even with flushing low, the biomass contained in the reactor can decrease, because the rate of formation for new biomass depends on the amount of substrate supplied and on the COD of the waste water. It is clear therefrom that the effective biomass retention is of decisive importance with respect to the performance of a biological reactor, in particular one such having an anaerobic biomass.

In known anaerobic reactors, owing to the intensive production of biogas, high upflow velocities of a plurality of m/h occur. If the microorganisms are not fixed to special supports by special culturing, the high upflow velocity causes a selection of species which form natural aggregates. This selection process is based on the fact that species that do not form aggregates are lighter, therefore are flushed from the reactor to a greater extent and are finally displaced by the aggregating species. This selection process extends over time periods of a plurality of months to some years and leads to the formation of a special sludge form which is generally termed granulated sludge or else "pellet sludge". The "sludge pellets" have a settling velocity in water of 50 to 150 m/h, whereas sludge flakes settle at approximately 1 m/h.

Typically, the sludge pellets are spherical or lens-shaped granules having grain sizes of approximately 0.5 to 2 mm. The sludge pellets consist of a porous lime framework which is formed in the course of the selection process. The bacteria in this process colonize not only the surface of the sludge pellets—for example in the case of solid closed support granules of a fixed-bed reactor—but may be also found on the internal surfaces of the lime framework.

Owing to the activity of the microorganisms, biogas is formed which firstly rises as gas bubbles, secondly also adheres to the biomass. Owing to the partial enveloping of the sludge pellets with biogas, the specific gravity of the sludge pellets falls below the density of water and the sludge pellets rise. The upwardly buoyant sludge pellets are collected by appropriately arranged gas hoods and there gradually release the gas again. The detachment of gas from the individual sludge pellets is reinforced by the upwardly decreasing hydrostatic pressure in the reactor, in that the gas is compressible and expands with a decreasing external pressure. The gas bubbles adhering to the sludge pellet become larger with decreasing pressure. The friction and sheer forces that act owing to the upward motion in the water thereby have a greater contact surface and the detachment of the gas bubble from the sludge pellet is promoted. Owing to the detachment of the gas from the individual sludge pellets, the specific gravity of the sludge pellets increases again, and so they fall back into the lower region of the reactor, where the process begins again. Owing to the formation of gas and the detachment of the gas from the sludge pellets, a cycle of floatation and sedimentation is in operation.

For the conversion of organic impurities, mass transport or diffusion at the surface of the sludge pellets plays a decisive role. The strength of the diffusion stream of a certain substance is proportional to the decrease in concentration thereof from the waste water to the microorganisms in the sludge pellet. The sludge pellet is in part surrounded by an envelope of adhering biogas. The decrease in concentration and the diffusion are inversely proportional to the thickness of this adherent gas envelope. The conversion of organic compounds and, in association therewith, the efficiency of the purification method, may be increased by detaching as quickly as possible the biogas envelope adhering to the sludge pellets. It is sufficiently known that the gas envelope adhering to the sludge pellets may be reduced by high turbulence, i.e. by high velocity gradients. However, in this case, it is necessary to take into account that excessive circulations in the reactor and the associated mechanical sheer forces can have a long-lasting effect on the growth process of the sludge pellets or prevent it. In an extreme case, the fragile granules can even be destroyed. Accordingly, effective circulation or recirculation of the biomass with gentle gas separation is desirable.

DE 10 2005 050 997 A1 discloses a method and a reactor for purifying waste water that is polluted with organic impurities, by means of an upflow anaerobic sludge blanket (UASB). The biomass present as sludge or sludge pellet suspension is circulated, wherein the proportion of recirculated biomass to total biomass in the reactor per day is greater than $0.1 \cdot d^{-1}$, in particular greater than $2 \cdot d^{-1}$, and particularly preferably greater than $10 \cdot d^{-1}$. The reactor comprises a reactor tank, conduits, a waste water mixer, a first flotation separator and at least one further floatation separator for separating reactor water, biomass and biogas, one or more mixers for mixing biomass and biogas, and a gas separator for separating biomass and biogas.

EP 0 170 332 A1 (whose United States equivalent is U.S. Pat. No. 4,609,460) discloses a method and a device for the anaerobic treatment of waste water by means of UASB, in which a vessel is used, into the lower region of which the waste water that is to be purified is passed and from the upper region of which the purified waste water is conducted away. In the vessel, anaerobic microorganisms are active. Between the waste water inlet and the overflow for the purified waste water, there are situated in the vessel gas collectors in the form of hoods, that are stacked one above the other, the upper region of which is connected via a conduit to a gas-sludge separation unit. By means of the activity of the microorganisms, gas is generated that is taken up by the sludge, and so this floats upwards as what is termed scum. This scum is collected by the hood and gradually releases its gas again, so that it again becomes heavier and sinks back to the bottom as what is termed bottom sludge. The gas released by the sludge pellets rises further upwardly in the lines together with the free gas bubbles collected by the hoods and entrains in the course of this scum particles and liquid which are separated off in the gas-sludge separation chamber. The gas is expediently removed, while the entrained liquid which can also contain sludge particles passes into a falling conduit which leads back to the bottom of the vessel. The bottom sludge by this means should be vortexed on the bottom, which leads to a loosening of the sludge zone in the bottom region and improved mixing of the microorganisms with the incoming waste water. However, since water is relatively heavy, the amount of the waste water that is transportable by the ascending gas and thereby also the vortexing performance of the recirculated waste water are limited. In addition, it is known that waste water reactors of this type must have reactor heights of at least 11 m before the effect described occurs.

EP 0 244 029 A1 (whose United States equivalent is U.S. Pat. No. 4,758,339) describes a UASB reactor which is equipped with a device for separating the three phases water, sludge and biogas. The separation device comprises gas hoods which are connected via passage openings to a gas collection box, wherein the passage openings are arranged in the upper region of the gas hoods below the top of the hood. In addition, each gas hood is equipped in the interior with retaining boxes. The retaining boxes and the passage opening are designed such that a gas cushion is formed which acts as a barrier to water and sludge.

WO 99/51532 (whose United States equivalent is U.S. Pat. No. 6,478,963B1) teaches a method and a device for the anaerobic purification of waste water in a vessel receiving waste water and sludge, with gas formation. The gas that forms is collected by a gas collector and the circuit driven by the ascending gas is used for loosening the bottom sludge that has sunk to the bottom of the vessel. Owing to a gas-lift effect of the ascending gas, the bottom sludge is removed from the bottom by suction and conducted separately from the waste water into the upper region of the vessel and hack into the waste water.

EP 0 711 732 A2 describes a module for a reactor for the anaerobic purification of waste water which contains an upper overflow threshold for the purified waste water that establishes the water level in the module, a plurality of collection hoods for biogas that are arranged staggered over the entire module cross section having an outlet into a gas collection space and an upper take off conduit for the exhaust air which is not collected by the take-off hoods. Above the respective floatation separator, the biogas is conducted into a gas collection chamber. The biogas is taken off from the collection hoods via a short pipe.

Studies have found that only 10 to 20% of the biomass present in a reactor actively participates in the purification process. 80 to 90% of the biomass present delivers virtually no contribution to the purification of the waste water. Accordingly, the recirculation of biomass and also the gentle separation of biogas is of decisive importance for the efficiency of biological methods, such as, for example, the UASB method.

The known biological reactors have a fixed geometry. After a start-up period of a plurality of weeks to months, stable operating conditions are established in the reactor, wherein the operating parameters fluctuate within method-specific process windows. The expression "process window" in this case designates associated ranges of the polydimensional space of the operating parameters which include, for example, the content and recirculation rate of the biomass in the reactor, the inflow amount, the chemical oxygen demand (COD), the temperature and the pH of the waste water fed. The process windows are substantially determined by the type of biomass used, the waste water supplied and the reactor parameters. In particular, the biomass recirculation that is important for reactor efficiency virtually cannot be controlled.

SUMMARY OF ADVANTAGEOUS EMBODIMENTS OF THE INVENTION

It is an object of the present invention to provide a reactor for the biological treatment of waste water with increased efficiency.

According to the invention the object above is achieved by an upflow reactor having the features of patent claim 1. The upflow reactor in question having recirculation of biomass comprises at least one first flotation separator which has one or more gas hoods connected to a collector, and is equipped with a device for controlling the recirculation of biomass.

In a preferred embodiment, the gas hoods of the first flotation separator comprise an outlet opening having controllable cross-sectional area.

Advantageous developments of the invention are characterized in that:
  the upflow reactor comprises at least one further or second flotation separator which is arranged above the first flotation separator and comprises one or more gas hoods connected to the collector;
  the gas hoods of the first and/or second flotation separator comprise an outlet opening having controllable cross-sectional area or variable geometry;
  the first and second flotation separators are of a type differing from one another, wherein the differing type can also result from differently selected or established geometries of the first and second flotation separators;
  at least one edge region of the outlet openings is restricted by a slideable diaphragm;
  the upflow reactor comprises actuators for actuating the slideable diaphragms, wherein the actuators are preferably equipped with a hydraulic drive;
  at least one edge region of the outlet opening is restricted by a flexible-tube diaphragm;
  the flexible-tube diaphragm is connected to pressure appliance for a fluid, preferably for water;
  the outlet opening is equipped with a siphon;

the siphon has a hood-like shape, wherein the siphon and the gas hood are preferably formed so as to be in one piece;

the siphon is formed so as to be tubular;

the upflow reactor comprises an electronic control;

the upflow reactor contains anaerobic and/or aerobic biomass.

BRIEF DESCRIPTION OF THE FIGURES

The invention will be described in more detail hereinafter with reference to drawings; in the drawings:

FIG. 2 shows an arrangement of the gas hoods first and a second flotation separator;

DETAILED DESCRIPTION OF ADVANTAGEOUS EMBODIMENTS OF THE INVENTION

Figure 1:
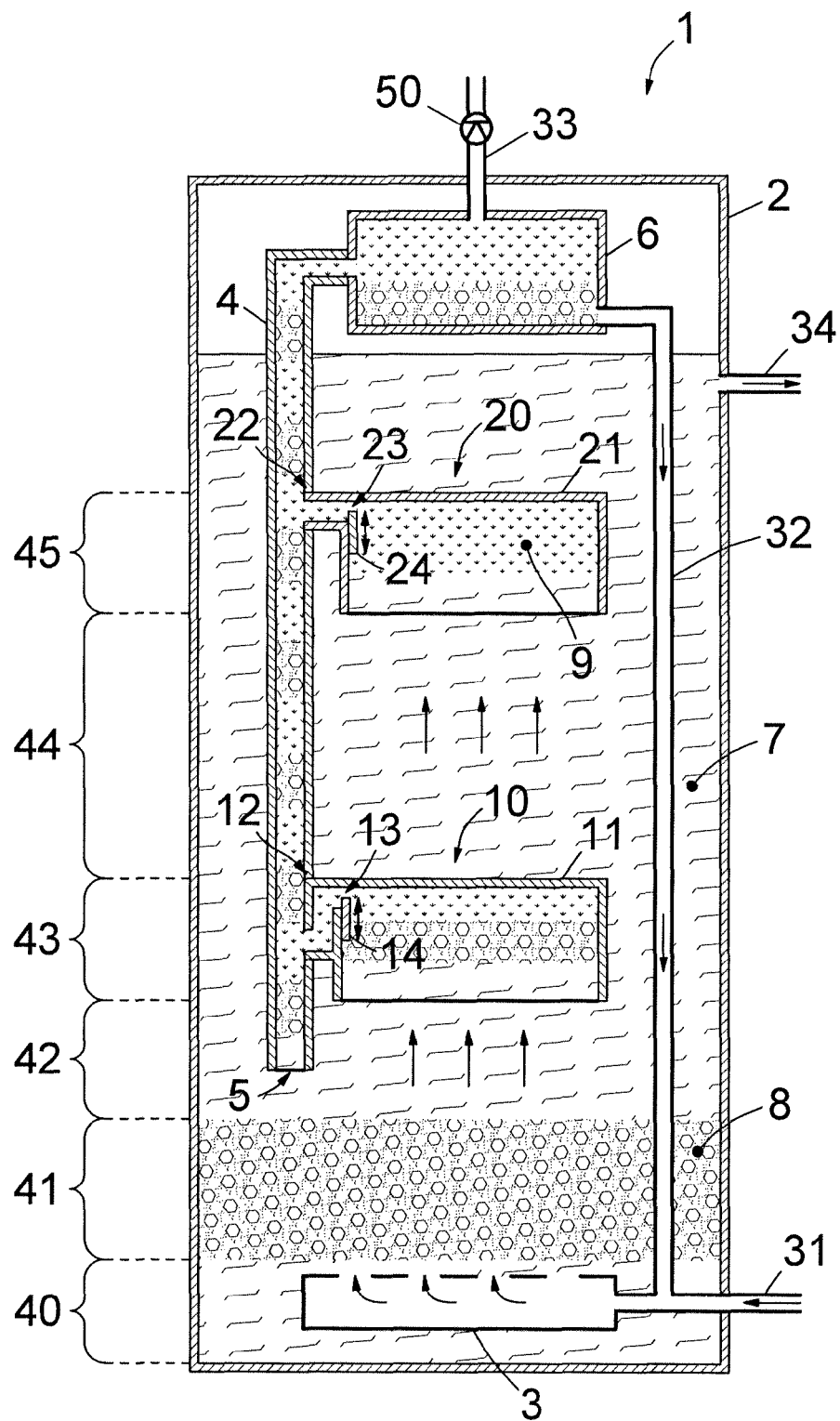
FIG. 1 shows a schematic sectional view of a reactor having recirculation of biomass.

FIG. 1 shows schematically an exemplary embodiment of an upflow reactor 1 according to the invention, comprising a reactor tank 2, conduits 31 to 34, a waste water distributor 3, a first and a second flotation separator 10, 20 for separating reactor water 7, biomass 8 and biogas 9, a collector 4 and a gas separator 6 for separating biomass 8 and biogas 9. The second flotation separator 20 is arranged vertically above the first flotation separator 10. Each flotation separator 10, 20 comprises at least one gas hood 11, 21 which is connected to the collector 4. Via the line 31, waste water is fed to the upflow reactor 1 and delivered by the waste water distributor 3 arranged in a bottom zone 40, with slight vortex formation, into a fermentation zone 41. Purified waste water is removed via the conduit 34 arranged in the upper region of the upflow reactor. In the fermentation zone 41, the biomass 8 is situated as a blanket of sludge or granular suspension. The bacteria contained in the biomass 8 degrade the organic components of the waste water, wherein biogas 9 is formed. In the fermentation zone 41, the biogas 9 in part goes in solution into the reactor water 7, and the other part forms fine bubbles which adhere to the biomass 8 or rise freely in the reactor water 7. The biomass 8 that participates in the formation of biogas 9, owing to the adhering biogas 9, becomes lighter than the reactor water 7 and likewise rises as do the free gas bubbles from the fermentation zone 41 into a first drift zone 42. The biogas 9 generated by the biomass 8 causes, together with the waste water that is fed via the conduit 31, an upwardly directed flow, not only of biomass 8, but also reactor water 7.

Above the first drift zone 42, there is arranged the first flotation separator 10 having one or more gas hoods 11 (see FIG. 2). The free bubbles of biogas 9 are trapped in the gas hoods 11 and form a gas cushion. Directly beneath the gas cushion a flotation layer forms consisting of biomass 8 interspersed with biogas 9.

Each gas hood 11, in an upper region, comprises an outlet opening 13, the width or cross-sectional area of which can be varied by means of one or more diaphragms 14. The outlet opening 13 opens out into a siphon 12. The siphon 12 is preferably constructed in a hood shape or tube shape, and opens out into the collector 4. Through the outlet opening 13 and the siphon 12, biogas 9 and biomass 8 flow from the gas hood 11 into the collector 4. On account of the deflection of the flow in the siphon 12, biomass 8 and biogas 9 are intensively mixed.

Preferably, the collector 4 is constructed as a vertically running box-shaped or tube-shaped riser conduit which is connected in a bottom region via an opening 5 to the interior space of the upflow reactor 1. Through the opening 5, reactor water 7 passes into the collector 4. The mix of biogas 9 and biomass 8 flowing into the collector 4 from the gas hoods 11 mixes with the reactor water 7 situated in the collector 4 and forms a mixture, the density of which is markedly lower than the density of the reactor water 7. On account of the density difference, the mixture rises upwards in the collector 4. The transport of the mixture of reactor water 7, biomass 8 and biogas 9 in the collector 4 is thus based on the known air-lift pump principle.

In an alternative embodiment of the invention, the collector 4, in a bottom region, preferably immediately beneath the outlet opening 13, is closed and is not directly connected to the interior space of the upflow reactor 1. In this embodiment, the air-lift pump effect is based on the density difference between biomass 9 and a mix of biomass 9 and biogas 8.

The majority of the floating biomass 8 interspersed with biogas 9 is collected in the floatation separator 10 and conveyed via the collector 4 to the gas separator 6. Reactor water 7 which flows round the gas hoods 11 of the floatation separator 10 and passes into a second drift zone 44, entrains only a small amount of floating biomass 8. In the drift zone 44, the hydrostatic pressure decreases continuously to about 1 atm. The biogas 9 adhering to the floating biomass 8 thereby forms bubbles which are increasingly larger and which finally detach. Owing to the detachment of the biogas 9, the specific gravity of the biomass 8 increases again, and so this falls back to the bottom of the reactor. The shielding by the first floatation separator 10 (see FIG. 2) in combination with the increased gas release in the drift zone 44 causes the reactor water 7 which passes to the surface of the water column in the reactor and is removed via the conduit 34 to be virtually free of biomass 8. The biogas 9 collected in the gas hoods 21 of the second floatation separator 20 flows through outlet openings 23 into the collector 4. In an advantageous development of the invention, one or more of the gas hoods 21 are each equipped with an adjustable diaphragm 24 and a siphon 22.

In the gas separator 6, the mix of biomass 8 and biogas 9 is separated, wherein the biomass 8 flows back under the action of gravity via the conduit 32 into the bottom region of the upflow reactor. Preferably, the conduit 32 is connected to the conduit 31, and so the recirculated biomass 8 is mixed with the supplied waste water.

The biogas 9 that is released in the gas separator 6 is removed via a conduit 33. Preferably, the volumetric flow rate of the biogas 9 that is removed via the conduit 33 is controllable via a throughput control valve 50 in the conduit 33. The pressure in the gas separator 6, and in association therewith, in the collector 4 and the gas hoods 11, 21 is controlled via the volumetric flow rate of the biogas 9 that is removed. By means of the throughput control valve 50, the thickness of the gas cushion in the gas hoods 11, 21 can therefore be controlled.

FIG. 2 shows a section transverse to the longitudinal axis of the flotation separator 10, 20. The gas hoods 11, 21 are preferably formed as hollow bodies having a polygonal or semi-circular casing wall, in particular in the form of an inverted V or inverted U having an opening 18 facing downward. As shown in FIG. 2, the gas hoods 11, 21 are arranged in two or more horizontal planes lying one above the other, in each of the flotation separators 10, 20. In one plane, the gas hoods 11, 21 are each parallel and arranged at a distance from one another. Rising reactor water 7 passes through the gap between adjacent gas hoods 11, 21 and flows upward. In each of the flotation separators 10, 20, the rows of gas hoods 11, 21 are offset to one another in planes lying one above the other, in such a manner that the vertical projections of the openings 18 of the gas hoods 11, 21 form a closed surface which partially or completely covers the internal cross section of the reactor tank 2. By means of this labyrinthine arrangement of the gas hoods 11, 21, biomass 8 and biogas 9 are virtually completely trapped.

Figure 3A:
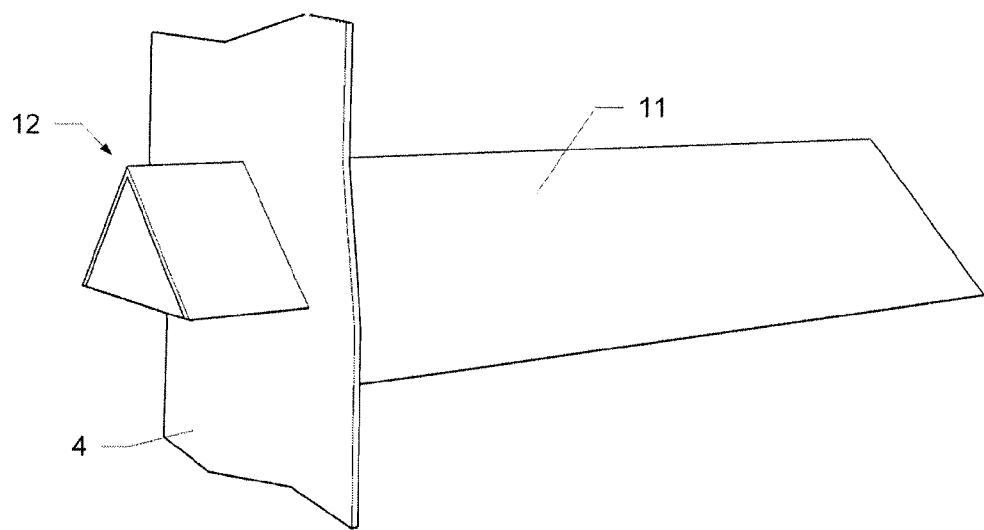
FIGS. 3a-b show a gas hood having a siphon, outlet opening and adjustable diaphragm in perspective view.
Figure 3B:
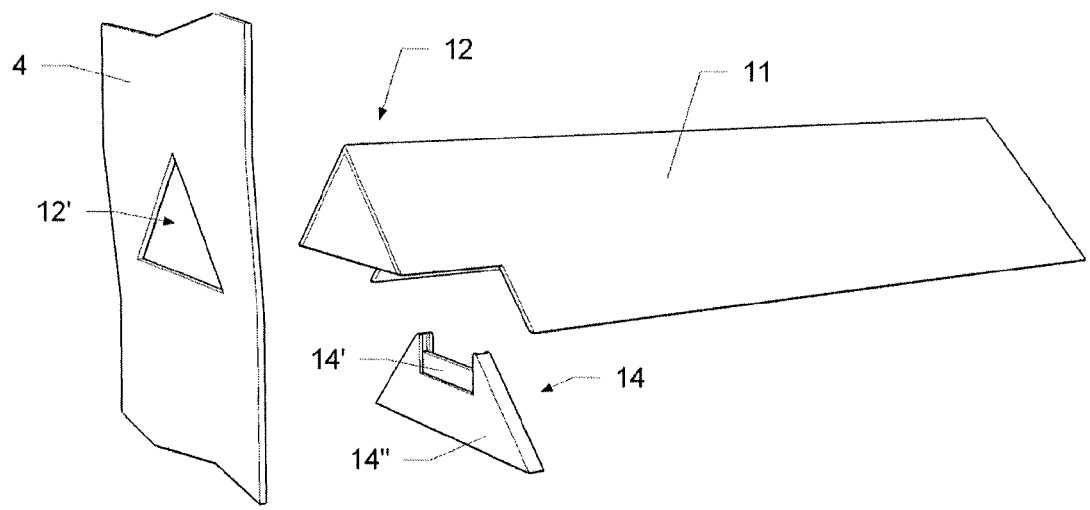

FIGS. 3a and 3b show in perspective view, and in exploded view, an exemplary embodiment of a gas hood 11 having a siphon 12, outlet opening 13 and controllable diaphragm 14. The diaphragm 14 is operated by means of an actuator—which is not shown in FIGS. 3a and 3b. The actuator is preferably equipped with a hydraulic drive, wherein water is particularly suitable as hydraulic fluid. Advantageously, the hydraulic drive comprises a cylinder having a slideable piston, wherein the cylinder is connected via a conduit, for example a flexible tube, to a pressure appliance or pump arranged outside the reactor tank 2.

Alternatively, or in supplementation to the embodiment shown in FIGS. 3a and 3b having a diaphragm 14 arranged below the outlet opening 13, the gas hood 11 can be equipped with one or more diaphragms arranged above and/or at the side of the outlet opening 13.

Figure 4A:
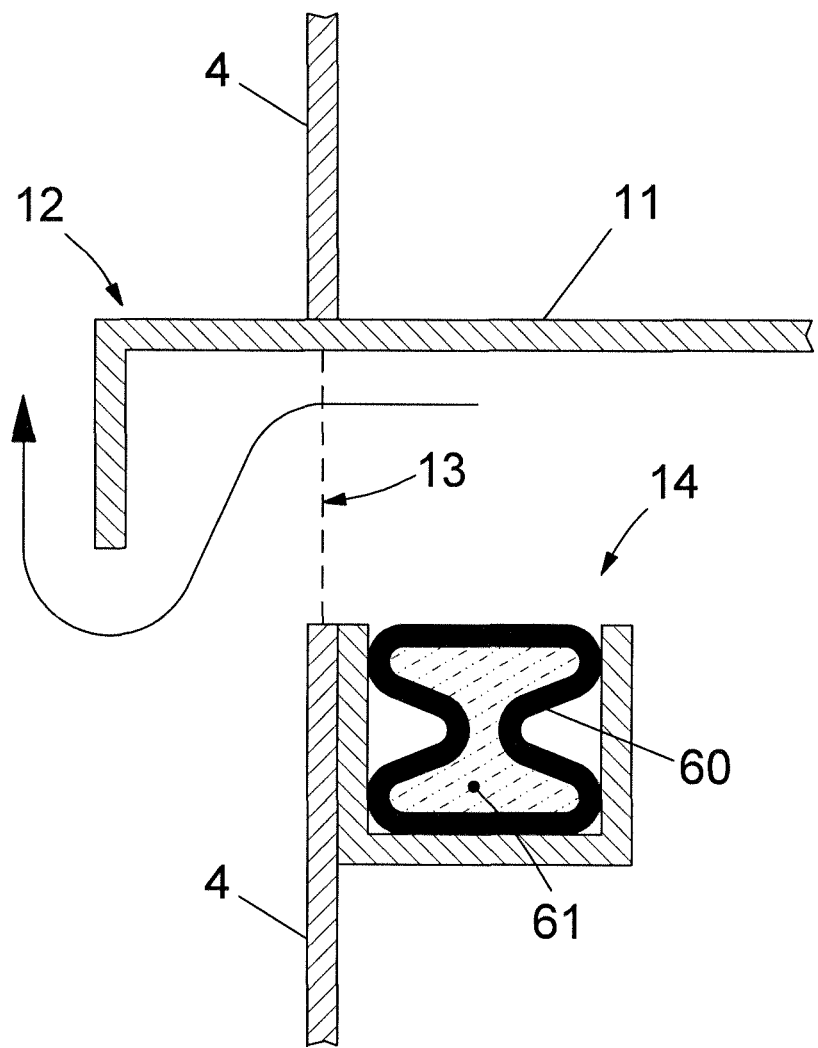
FIGS. 4a-b show an outlet opening having a flexible-tube diaphragm.
Figure 4B:
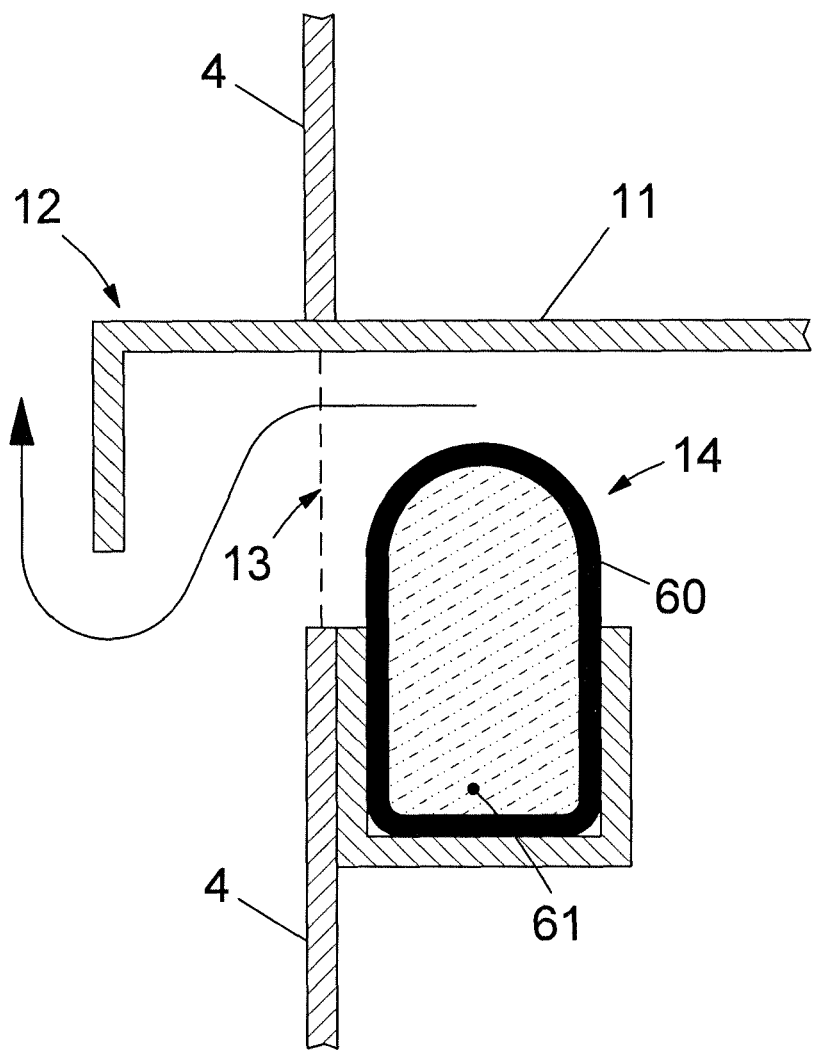

In an advantageous development of the invention, the adjustable diaphragms 14 are constructed as flexible-tube diaphragms. FIGS. 4a and 4b show an example of flexible-tube diaphragm 14 according to the invention, schematically in sectional view. The flexible-tube diaphragm 14 comprises a tubular hollow body 60 closed fluid-tightly, that is made of an elastic material such as, for example, rubber. The interior space of the hollow body 60 is connected to a pressure appliance, such as a pump (which is not shown in FIGS. 4a and 4b). By means of the pressure appliance, the elastic hollow body 60 is charged with a predetermined amount of a fluid 61, which is preferably water. Depending on the fill quantity of the fluid 61, the flexible-tube diaphragm 14 is open to a greater or lesser extent.

In a further embodiment of the invention, the diaphragms 14, 24 and the flotation separators 10, 20 are equipped with mechanical actuators, for example a linear guide with spindle drive, which are actuated manually or by means of a motor. In particular for manual actuation, the mechanical actuators of the diaphragms 14 are coupled to shafts, wherein the shafts are conducted liquid-tightly through the wall of the reactor tank 2 and are therefore accessible from the outside.

Figure 5:
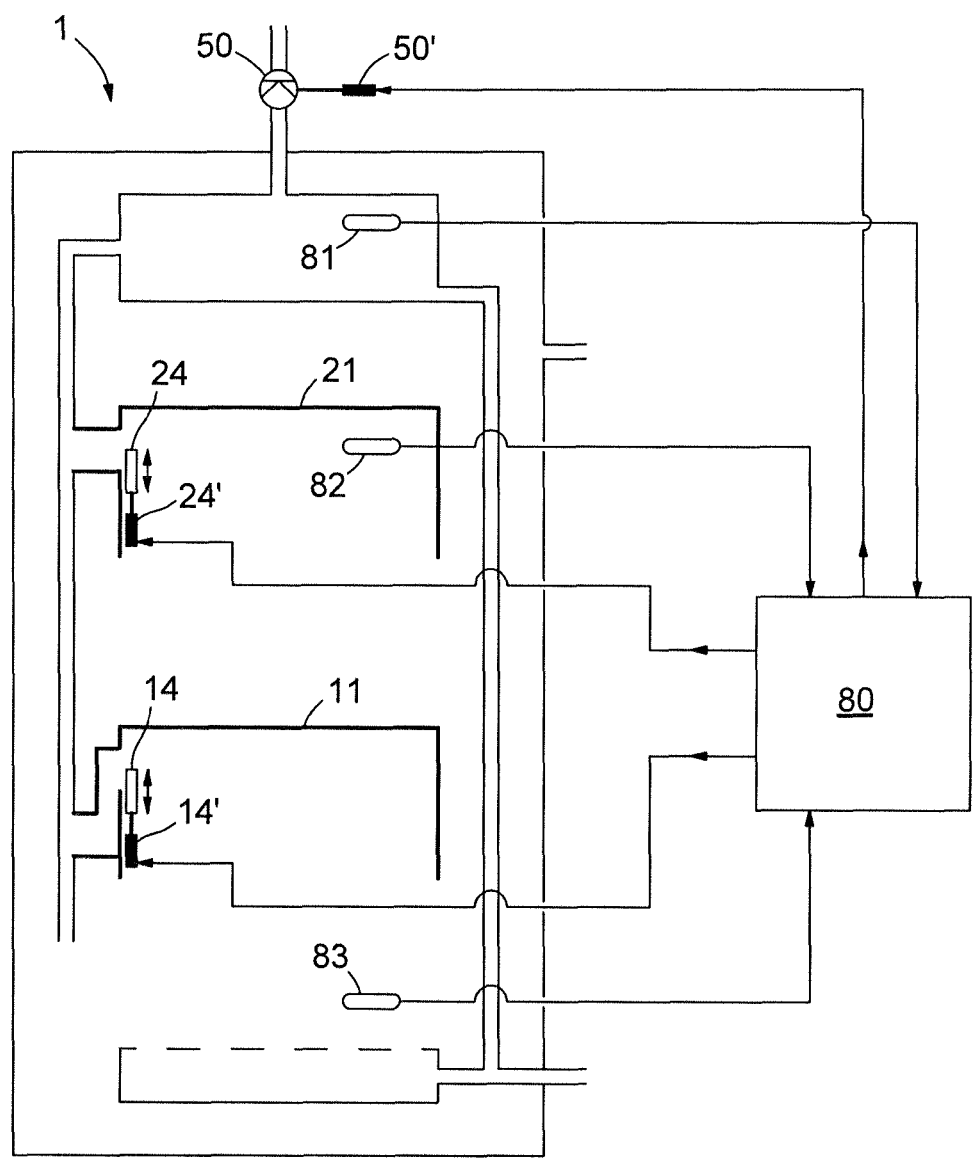
FIG. 5 shows an electronic control for the slideable diaphragms.

FIG. 5 schematically shows an exemplary embodiment of the invention in which the upflow reactor 1 comprises an electronic control 80 and one or more sensors and also one or more actuators. The sensors are, for example, pressure, temperature, oxygen or pH sensors, which can be mounted at various positions in the upflow reactor 1. The sensors are denoted in FIG. 5 with the reference signs 81, 82 and 83, and the actuators with 14', 24', 50'. The actuators 14', 24', 50' comprise generally an electric or hydraulic drive and serve preferably for positioning the diaphragms 14, 24 and the flow control valve 50. The control 80 has a signal input for each of the sensors 61, 62, 63 and a control output for each of the actuators 14', 24', 50' The control 80 is advantageously constructed as a stored program system (SPS). In the SPS store, a programmed algorithm of the control loop type is stored, by means of which the control signals for the actuators 14', 24', 50' are calculated in dependence on the signals of the sensors 61, 62, 63.

The invention claimed is:

1. An upflow reactor having recirculation of biomass for the biological treatment of waste water having at least one first flotation separator which comprises one or more gas hoods connected to a collector wherein the upflow reactor is equipped with a device for controlling the recirculation of the biomass, and the gas hoods comprise an outlet opening having a controllable cross-sectional area or geometry.

2. The upflow reactor as claimed in claim 1, wherein the upflow reactor comprises a second flotation separator which is arranged above the first flotation separator and comprises one or more gas hoods connected to the collector.

3. The upflow reactor as claimed in claim 2, wherein the second-flotation-separator gas hoods comprise an outlet opening having a controllable cross-sectional area or geometry.

4. The upflow reactor as claimed in claim 2, wherein the first flotation separator and the second flotation separator are of a type differing from one another.

5. The upflow reactor as claimed in claim 3, wherein at least one edge region of the outlet openings is restricted by a slideable diaphragm.

6. The upflow reactor as claimed in claim 4, wherein the upflow reactor comprises actuators for actuating the slideable diaphragms.

7. The upflow reactor as claimed in claim 3, wherein at least one edge region of the outlet opening is restricted by a flexible-tube diaphragm.

8. The upflow reactor as claimed in claim 7, wherein the flexible-tube diaphragm is connected to a pressure appliance for a fluid.

9. The upflow reactor as claimed in claim 3, wherein the outlet opening is equipped with a siphon.

10. The upflow reactor as claimed in claim 9, wherein the siphon is constructed in a hood-shape.

11. The upflow reactor as claimed in claim 10, wherein the siphon and the gas hood are formed so as to be in one piece.

12. The upflow reactor as claimed in claim 9, wherein the siphon is formed so as to be tubular.

13. The upflow reactor as claimed in claim 1, wherein the upflow reactor comprises an electronic control.

14. The upflow reactor as claimed in claim 1, wherein the upflow reactor contains anaerobic and/or aerobic biomass.

15. The upflow reactor as claimed in claim 6, wherein the actuators are equipped with a hydraulic drive.

16. The upflow reactor as claimed in claim 8, wherein the fluid is water.

\* \* \* \* \*

UNITED STATES PATENT AND TRADEMARK OFFICE
CERTIFICATE OF CORRECTION

| | | |
|---|---|---|
| PATENT NO. | : 8,721,877 B2 | |
| APPLICATION NO. | : 13/132928 | |
| DATED | : May 13, 2014 | |
| INVENTOR(S) | : Marianne Buchmueller | |

It is certified that error appears in the above-identified patent and that said Letters Patent is hereby corrected as shown below:

In the claims

In Column 8, Line 33, change "4" to --5--.

Signed and Sealed this
Fifteenth Day of July, 2014

Michelle K. Lee
*Deputy Director of the United States Patent and Trademark Office*